United States Patent [19]

Dewald et al.

[11] 4,059,642
[45] Nov. 22, 1977

[54] PREFERENTIAL ALKYLATION OR ACYLATION OF META-DISUBSTITUTED BENZENES

[75] Inventors: James R. Dewald, Bay City, Mich.; Lowell D. Markley, Clayton, Calif.

[73] Assignee: The Dow Chemical Company, Midland, Mich.

[21] Appl. No.: 707,924

[22] Filed: July 22, 1976

[51] Int. Cl.$^2$ ............................................. C07C 25/08
[52] U.S. Cl. ................................................ 260/650 R
[58] Field of Search ................................... 260/650 R

[56] References Cited

U.S. PATENT DOCUMENTS 3,358,046  12/1967  Offenhauer et al. ............. 260/650 R

OTHER PUBLICATIONS

Olah et al., Aromatic Substitution XVIII, Friedel–Crafts t-Butylation of Benzene and Methylbenzenes with t-Butyl Bromide and Isobutyleen; JACS; 86; 3-2-0-64; p. 1060.

*Primary Examiner*—Herbert Levine
*Assistant Examiner*—J. Thierstein
*Attorney, Agent, or Firm*—Michael S. Jenkins

[57] ABSTRACT

In a mixture of isomers of a disubstituted benzene such as dichlorobenzene, the meta-disubstituted isomer is preferentially reacted with an alkylating or acylating agent, e.g., an alkyl halide, by contacting the mixture with the agent in the presence of a Friedel-Craft catalyst at a temperature of less than about 60° C.

The resulting alkylated or acylated meta-isomer can be readily separated from the reaction mixture by simple distillation.

11 Claims, No Drawings

PREFERENTIAL ALKYLATION OR ACYLATION OF META-DISUBSTITUTED BENZENES

BACKGROUND OF THE INVENTION

This invention relates to a process for the preferential alkylation or acylation of a meta-disubstituted benzene.

Processes for the preparation of meta-disubstituted benzenes, particularly meta-dichlorobenzene, are known in the art. Unfortunately, since very little meta-dichlorobenzene is produced by the direct chlorination of benzene, meta-dichlorobenzene is commonly prepared by indirect routes, e.g. from meta-dinitrobenzene or meta-chloronitrobenzene. A process often used is a complex one involving the reduction of nitro groups to amino groups followed by diazotization and treatment of the diazonium salt with cuprous chloride. Meta-dichlorobenzene produced this way is expensive primarily because product yield in the multi-step process is low.

Recently, a method for producing meta-dichlorobenzene from benzene was disclosed in U.S. Pat. No. 3,358,046 to Offenhauer and Rodewald. In the practice of this method, the benzene ring is first alkylated and then chlorinated to form an ar,ar-dichloro-ar-alkylbenzene in which the chloro groups are meta to each other. The resulting compounds are then dealkylated to give the desired meta-dichlorobenzene. Unfortunately, catalyst requirements for the alkylation step are generally excessive, e.g., on the order of about 25 weight percent based on the aromatic substrate. Also, it is generally necessary to place at least two and often three alkyl groups on each aromatic ring to be chlorinated in order to obtain the desired meta-substitution of the chloro groups. Accordingly the demand for alkylating agent is also excessive.

In view of the several undesirable aspects of the aforementioned prior art processes, it would be highly desirable to provide a process for making meta-dihalobenzenes requiring lesser amounts of aluminum trichloride catalyst and alkylating agent. More broadly, it would be desirable to provide a process for making meta-disubstituted benzenes and for preferentially alkylating or acylating such meta-disubstituted benzenes.

SUMMARY OF THE INVENTION

Accordingly, this invention relates to a process for the alkylation or acylation of a meta-disubstituted benzene in an isomeric mixture containing meta-disubstituted benzene and para-disubstituted benzene which process comprises contacting the isomeric mixture with an alkylating or acylating agent in the presence of a catalytic amount of a Friedel-Crafts catalyst at a reaction temperature less than about 60° C such that the meta-disubstituted benzene is preferentially alkylated or acylated. The above preferential reaction is unique in that, at the particular temperature employed, usually less than two mole percent of the para-disubstituted benzene is alkylated or acylated while essentially all of the meta-disubstituted benzene is.

If essentially pure meta-disubstituted benzene is desired, the alkylated meta-disubstituted benzene is first separated from remaining non-alkylated isomers by a simple distillation procedure. Thereafter, the recovered alkylated meta-disubstituted benzene is dealkylated by known procedures, e.g., as described in U.S. Pat. No. 3,358,046, Column 3, line 65 to Column 4, line 13.

The meta-disubstituted benzenes as well as the acylated or alkylated products are useful precursors in the synthesis of other organic compounds. For example, meta-dichlorobenzene can be hydrolyzed to meta-chlorophenol and resorcinol which are useful in the production of synthetic resins and explosives.

DETAILED DESCRIPTION OF THE INVENTION

The essential starting materials for the practice of the preferential acylation or alkylation (hereinafter called the preferential reaction) are three: an isomeric mixture, an alkylating or acylating agent, and a Friedel-Crafts catalyst.

The isomeric mixture advantageously contains meta-disubstituted benzene (formula I) and para-disubstituted benzene (formula II).

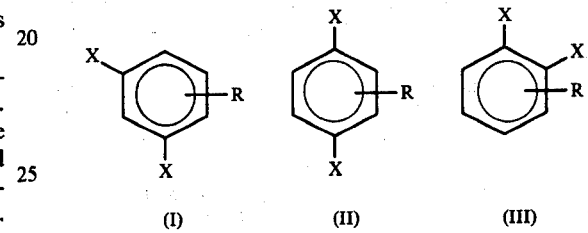

(I)  (II)  (III)

The isomeric mixture generally contains essentially no ortho-disubstituted benzene (formula III) since the ortho-disubstituted benzene can be and is normally separated from the meta- and para-disubstituted benzenes by simple distillation prior to further processing. Moreover such prior separation of the ortho-isomer in this case is particularly advantageous since the ortho-isomer tends to alkylate or acylate almost as easily as the meta-disubstituted isomer. In formulas I, II, and III, X is individually a halogen, preferably Br and Cl, and most preferably Cl. For the purposes of this invention, it is understood that the term "disubstituted" includes isomers in which a third group, an R group, is present on the ring. The R group is advantageously hydrogen or an alkyl containing from one to about eight carbon atoms, preferably containing from about two to about six, and most preferably containing three carbon atoms. When R is alkyl, it is normally positioned on the ring of formula I to give a 2,4-disubstituted-1-alkylbenzene which can be readily alkylated or acylated by the process of this invention. On the other hand, it is observed that the 3,5-disubstituted-1-alkylbenzene does not alkylate or acylate appreciably under the conditions of this process. While R may be in any available ring position in the isomers of formulas II or III, R is normally positioned in isomer II to provide 2,5-disubstituted-1-alkylbenzene.

The isomeric mixture can be prepared in any of a number of ways. The preferred method is isomerization of other disubstituted benzenes (ortho- or para-disubstituted benzenes or a mixture of the two). Para-disubstituted benzenes of formula II (wherein X and R are as previously defined) and ortho-disubstituted benzenes of formula III can be used.

The isomerization reaction is typically conducted by contacting ortho- or para-disubstituted benzenes or mixture thereof with aluminum trichloride to form a mixture containing ortho-, meta-, and para-disubstituted benzenes. Such suitable isomerization processes are more completely described in the prior art, for example, U.S. Pat. No. 2,819,321. As taught therein, a mixture of ortho- and para-dichlorobenzenes can be isomerized in relatively high conversion to the meta-isomer by heating them to at least 120° C in the presence of aluminum chloride and anhydrous hydrogen chloride and under superatmospheric pressures from 650 to 1500 pounds per square inch gauge (psig). The relative concentration of isomers in the mixture is not important.

The isomerized mixture is then separated into two fractions, usually by simple distillation. The first fraction is an isomeric mixture of meta- and para-disubstituted benzenes and the second fraction contains ortho-disubstituted benzene. The first fraction is suitably employed as the substrate reactant (isomeric mixture) in the preferential alkylation or acylation reaction.

The second essential starting material for the practice of the preferential reaction is an alkylating or an acylating agent (hereinafter referred to as agent). In the alkylation or acylation of dihalobenzenes, agents suitable for use in the preferential reaction include hydrocarbyl halides, such as alkyl halides or alkaryl halides, olefins, alkyl alcohols and acid halides, advantageously those which are capable of forming a secondary carbonium ion but which do not normally form a tertiary carbonium ion. Exemplary alkyl halides include isopropyl chloride, n-propyl bromide, s-butyl chloride, 2- or 3-pentyl chloride and other primary or secondary alkyl halides having 3 to 5 carbon atoms. Preferred are those alkyl halides wherein alkyl is linear (not branched). Exemplary alkaryl halides include 2,4-dichloro-5-isopropylcumene, 2,4-dichloro-5-(s-butyl)cumene, 2,4-dichloro-3-isopropyl cumene, and others as represented by the formula:

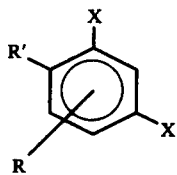

wherein X and R are as defined hereinbefore and R' is an alkyl group, preferably a linear alkyl group, having from 3 to 5 carbon atoms. Of the foregoing alkaryl halides, the 2,4-dichloro-1,5-dialkylbenzenes are preferred, with the most preferred being those wherein alkyl is isopropyl.

Exemplary olefins include propylene, 1- or 2-butene, 1- or 2-pentene and the like, preferably linear olefins. Exemplary alkyl alcohols include isopropyl alcohol, 1- or 2-butanol and others having from 3 to 5 carbons, preferably those wherein alkyl is linear. Exemplary acid halides include acetyl chloride, propionyl chloride, butyryl chloride and others having 3 to about 5 carbon atoms and of the formula R"COX wherein R" is alkyl and X is halogen, preferably Cl. The aforementioned alkylating agents are preferred over acylating agents because of the facility with which they can be removed from the alkylated product. Of the foregoing alkylating agents, the alkaryl halides are especially preferred due to their high selectivity for the alkylation of the meta-disubstituted benzene of formula I. The agents usable in the alkylation or acylation of dihalobenzenes are likewise usable in the alkylation or acylation of ar, ar-dihalo-ar-alkylbenzenes.

However, additional suitable agents applicable in the latter case include hydrocarbyl halides, such as alkyl halides, olefins, alkyl alcohols, and acid halides which are capable of forming a tertiary carbonium ion. Exemplary halides include t-butyl chloride, 2-chloro, 2-methyl butane and other alkyl chlorides containing from 3 to about 10 carbon atoms. Exemplary olefins include isobutylene, 2-methyl-1-butene, and other olefins having from 3 to about 10 carbon atoms. Exemplary alcohols include t-butanol, 2-methyl, 2-hydroxy butane, and other alcohols having from 3 to about 10 carbon atoms.

Agents are typically employed in the preferential reaction at a ratio of between about one to about 10 moles of compound of formula I per mole of agent. In order to maintain the selectivity of the reaction, it is desirable to maintain the ratio higher than one mole of compound of formula I per mole of agent. Therefore such agents are preferably employed in an amount to provide a ratio of about three to about five, most preferably three, moles of compound of formula I per mole of agent.

The third essential starting material for the practice of the preferential reaction is a catalyst. In the alkylation or acylation of dihalobenzenes (e.g., when the R of formulas I, II, and III is hydrogen), usable catalysts include aluminum halides, preferably aluminum trihalides, and most preferably aluminum trichloride. Other catalysts include aluminum tribromide and the like. Catalysts usable in the alkylation or acylation of dihalobenzenes are also usable in the alkylation or acylation of ar, ar-dihalo-ar-alkylbenzenes (e.g., when the R of formulas I, II, and III is alkyl). However, additional suitable catalysts applicable in the latter case include Friedel-Crafts catalysts such as sulfuric acid, $FeCl_3$, $SnCl_4$, $TiCl_4$, and $SbCl_3$.

In the preparation for the preferential reaction, a mixture is formed of the catalyst and the isomeric mixture. Agitation sufficient to keep the catalyst and the mixture intimately mixed by, for example, stirring is conducted throughout the reaction. The catalyst should be present in a catalytic amount. In the alkylation of the dihalobenzenes such a catalytic amount is between about 0.05 weight percent and about 5.0 weight percent, and preferably between about 0.5 percent and about 1.5 weight percent, based on the weight of the isomeric mixture. In the alkylation of ar, ar-dihalo-ar-alkylbenzenes, such catalytic amounts range from about one to about ten weight percent, preferably from about two to about five weight percent, based on the isomeric mixture.

Advantageously after the catalyst and isomeric mixture are combined, the agent is added in metered amounts to the mixture of catalyst and isomers in order to control the heat of reaction as the substitution product is formed. During the reaction, the reaction mixture should be maintained at a temperature below about 60° C, advantageously at a temperature of between about −20° C and about 60° C, and preferably between about −20° C and about 20° C. While reaction pressure is not critical, pressures between about 0 psig and about 5 psig while venting the reactor are advantageously employed. To assure complete reaction, the mixture is stirred for a period of time sufficient to assure complete reaction. Upon completion of the reaction, a quantity of water sufficient to destroy any residual catalyst is added.

The substitution product is then separated from the para-disubstituted benzene. Although not critical, this separation is typically accomplished by simple distillation.

The meta-isomer is optionally regenerated in an abstraction step which comprises contacting the alkylated meta-isomer with a suitable dealkylation catalyst, e.g., activated or calcined aluminas and activated bauxites, aluminum chloride catalysts or similar dealkylation catalyst. A suitable abstraction process is taught in U.S. Pat. No. 2,979,536.

The meta-isomer is recovered from the reaction products of the abstraction reaction by a conventional technique, e.g., distillation.

The following examples is given to illustrate the invention and should not be construed as limiting its scope. All percentages in the examples are by weight unless otherwise indicated.

EXAMPLE 1

An isomeric mixture of ortho-, meta- and para-dichlorobenzenes prepared in a conventional manner, e.g., Example 1 of U.S. Pat. No. 2,819,321, is placed in a distillation apparatus and the meta- and para-isomers are distilled from the remaining mixture by a simple distillation procedure. The relative proportions of the isomers recovered by the distillation are 62.3 percent meta-dichlorobenzene and 37.7 percent para-dichlorobenzene.

To effect a separation of the meta-isomer from the para-isomer, the two isomers (212.8 g.) and 0.56 percent (1.2 g.) of $AlCl_3$ are placed in a three-necked flask equipped with cooling means, a thermometer, a graduated feed reservoir having a stopcock, an electric stirrer, and a dry ice condenser. Isopropyl chloride (32.4 g.) is placed in the graduated feed reservoir which is inserted into one of the necks of the three-necked flask such that the isopropyl chloride can feed into the flask below the level of liquid ingredients therein. The second neck admits the stirring rod. The third neck is fitted with the dry ice condenser to prevent escape of reactants and products as vapor. The thermometer is inserted periodically through one of the necks.

The reaction is begun by stirring the contents of the flask and adding the isopropyl chloride dropwise to the contents of the flask over a period of 30 minutes. Temperature of the reaction mixture is maintained at 20° C throughout the reaction which is carried out at atmospheric pressure. Evolution of HCl gas indicates that reaction occurs. To assure complete reaction, the mixture is stirred for 15 minutes after all the isopropyl chloride is added. To destroy any residual catalyst, about 10 ml of water is added. An organic layer weighing 221.0 g is removed and fractionally distilled.

A forty-six gram-cut is recovered, analyzed by gas liquid chromatography and found to contain 99.7 weight percent of alkylated product. This alkylated product is identified as 2,4-dichlorocumene by comparison with an authentic standard. Further analysis indicates that less than one percent 2,5-dichlorocumene is present in the organic layer. Analysis of the 2,4-dichlorocumene by gas liquid chromatography reveals it to be 99.7 percent pure.

The minimal amount of 2,5-dichlorocumene produced in this preferential alkylation reaction illustrates the high selectivity of the present invention for meta-dichlorobenzene.

To obtain meta-dichlorobenzene, the 2,4-dichlorocumene is dealkylated according to a conventional dealkylation procedure, e.g., as described in U.S. Pat. No. 3,358,046, Column 4, line 69 – Column 5, line 13.

EXAMPLE 2

Generally following the procedure of Example 1, an isomeric mixture (231 parts) of 45 percent 2,4-dichlorocumene and 55 percent 3,5-dichlorocumene is mixed with 2.5 parts anhydrous aluminum chloride at 25°–40° C for 20 minutes. A 48-part portion of isopropyl chloride is then added dropwise over a period of one hour to the aforementioned mixture while stirring the mixture and maintaining the temperature of the reaction mixture at 25°–40° C. The mixture is stirred at 25° to 40° C for an additional half hour and 40 parts of water is added to destroy the catalyst. The resulting mixture, which is allowed to stand for 1-2 hours without agitation, separates into two layers. The lower product layer is then recovered and distilled, using a 10-plate column and a pressure of 10–40 mm Hg. A 115-part portion of 3,5-dichlorocumene (b.p. 119° C/25 mm Hg), is recovered as the overhead product. This recovery of product represents a 90.5 percent yield based on available 3,5-dichlorocumene. Analysis of the recovered distillate indicates a constituency as follows:

94–98 percent 3,5-dichlorocumene
1–3 percent 2,4-dichlorocumene
1–3 percent 2,4-dichloro-5-isopropylcumene
0.5 percent unknown.

Analysis of the remaining pot residue from the aforementioned distillation indicates 142 parts of a mixture of 91.5 percent 2,4-dichloro-5-isopropylcumene. and 8.5 percent 3,5-dichlorocumene.

As evidenced by the foregoing results, essentially all of the 2,4-dichlorocumene alkylates whereas very little of the 3,5-dichlorocumene does, thus further illustrating the preferential alkylation characteristics of the novel process disclosed herein.

What is claimed is:

1. In an isomeric mixture comprising para- and meta-disubstituted benzenes having two halogen substituents, a process for the alkylation of the meta-disubstituted benzene which process comprises contacting the isomeric mixture with an alkylating agent in the presence of a catalytic amount of a Friedel-Crafts catalyst at a reaction temperature less than about 60° C such that the meta-disubstituted benzene is preferentially alkylated.

2. In an isomeric mixture comprising disubstituted benzenes represented by the formulas:

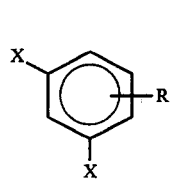 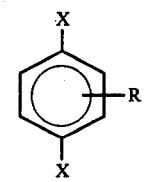

(I)         (II)

wherein each X is individually halogen and R is hydrogen, a process for the preferential alkylation of the disubstituted benzene of formula (I) which process comprises contacting the isomeric mixture with an alkylating agent in the presence of a catalytic amount of an aluminum trihalide at a reaction temperature of between about −20° C and about 60° C.

3. In an isomeric mixture comprising disubstituted benzenes represented by the formulas:

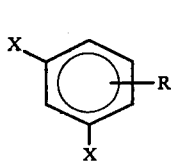 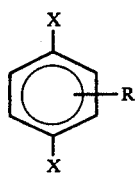

(I)  (II)

wherein each X is individually halogen and R is alkyl, a process for the preferential alkylation of the disubstituted benzene of formula (I) which process comprises contacting the isomeric mixture with an alkylating agent in the presence of a catalytic amount of a Friedel-Crafts catalyst at a reaction temperature of between about −20° C and about 60° C.

4. The process of claim 3 wherein the R group of formula (I) is alkyl and is positioned to give a 2,4-disubstituted-1-alkylbenzene and the R group of formula (II) is alkyl and is positioned to give a 2,5-disubstituted-1-alkylbenzene.

5. The process of claim 3 wherein R contains three carbon atoms.

6. The process of claim 2 wherein the alkylating agent is selected from the group consisting of
 a. linear alkyl halides having three to about five carbon atoms,
 b. linear olefins having three to about five carbon atoms,
 c. linear alkyl alcohols having three to about five carbon atoms,
 d. 2,4-dichloro-1,5-dialkylbenzene wherein alkyl has from three to about five carbon atoms.

7. The process of claim 3 wherein the alkylating agent is selected from the group consisting of
 a. alkyl halides having from three to about 10 carbon atoms,
 b. olefins having from three to about 10 carbon atoms, and
 c. alkyl alcohols having from three to about 10 carbon atoms.

8. The process of claim 2 wherein the alkylating agent is isopropyl chloride or 2,4-dichloro-5-isopropylcumene.

9. The process of claim 2 wherein X is Cl and preferential alkylation is accomplished with an alkylating agent of isopropyl chloride in the presence of between about 0.5 and 1.5 weight percent aluminum trichloride at a temperature of between about −20° C and about 20° C.

10. The process of claim 3 wherein X is Cl and preferential alkylation is accomplished with an alkylating agent of 2,4-dichloro-5-isopropylcumene in the presence of between about 2 and about 5 weight percent aluminum trichloride at a temperature of between about −20° C and about 20° C.

11. In an isomeric mixture comprising para- and m-dihalobenzenes, a process for the alkylation of the m-dihalobenzene which process comprises contacting the isomeric mixture with an alkylating agent in the presence of a catalytic amount of a Friedel-Crafts catalyst at a reaction temperature less than about 60° C such that the m-dihalobenzene is preferentially alkylated.

* * * * *

UNITED STATES PATENT AND TRADEMARK OFFICE
CERTIFICATE OF CORRECTION

PATENT NO. : 4,059,642
DATED : November 22, 1977
INVENTOR(S) : James R. Dewald; Lowell D. Markley It is certified that error appears in the above-identified patent and that said Letters Patent are hereby corrected as shown below:

Column 4, line 1, after "plary" insert --alkyl--;

Column 4, line 33, after "In" delete "the";

Column 6, line 31, before "and" delete the period ".";

Column 7, line 11, after "alkyl," insert --and wherein the R group of formula (I) is positioned to give a 2,4-disubstituted-1-alkylbenzene and the R group of formula (II) is positioned to give a 2,5-disubstituted-1-alkylbenzene,--;

Column 7, delete Claim 4.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks